(12) United States Patent
Chang et al.

(10) Patent No.: US 10,610,448 B2
(45) Date of Patent: Apr. 7, 2020

(54) SPA APPARATUS

(71) Applicants: Hui-Mei Chang, Taichung (TW); Tsair-Rong Chen, Changhua (TW)

(72) Inventors: Hui-Mei Chang, Taichung (TW); Tsair-Rong Chen, Changhua (TW)

(73) Assignees: Yi Jin Shiuan Beauty Co. Ltd., Taichung (TW); Dept. of Electrical Engineering, National Changhua University of Education, Changhua (TW)

(*) Notice: Subject to any disclaimer, the term of this patent is extended or adjusted under 35 U.S.C. 154(b) by 49 days.

(21) Appl. No.: 15/991,968

(22) Filed: May 29, 2018

(65) Prior Publication Data

US 2019/0365601 A1    Dec. 5, 2019

(51) Int. Cl.
| | |
|---|---|
| *A61H 33/00* | (2006.01) |
| *A61H 35/00* | (2006.01) |
| *A61Q 19/08* | (2006.01) |
| *A61N 5/06* | (2006.01) |

(52) U.S. Cl.
CPC ........... *A61H 33/60* (2013.01); *A61H 35/008* (2013.01); *A61Q 19/08* (2013.01); *A61H 33/0087* (2013.01); *A61N 5/0616* (2013.01)

(58) Field of Classification Search
CPC ....... A61H 33/60; A61H 35/008; A61Q 19/08
USPC ................................................ 4/541.1–541.5
See application file for complete search history.

(56) References Cited

U.S. PATENT DOCUMENTS

2017/0246474 A1* 8/2017 Schanze ............... A61N 5/0616

* cited by examiner

*Primary Examiner* — Christine J Skubinna
(74) *Attorney, Agent, or Firm* — Che-Yang Chen; Law Offices of Scott Warmuth

(57) ABSTRACT

A spa apparatus may comprise a cart, a magnifying lamp, a phototherapy mask, a bed, and a bathtub. A computer, a storage battery, and a communicator are electrically connected and installed inside the cart, and the cart is electrically connected to a power outlet and a display, which enables the cart to be moved and used not limited by the location of power supply. Moreover, the cart has a drawer and a spacing for the storage of beauty products and tools, and through sequentially connecting to a front arm, a rear arm, and a base, the phototherapy mask is configured to be used in different angles and to be held above or in front of a user's in a preferable height.

10 Claims, 9 Drawing Sheets

SPA APPARATUS

FIELD OF THE INVENTION

The present invention relates to a spa apparatus and more particularly to a high-efficiency spa apparatus.

BACKGROUND OF THE INVENTION

Nowadays, beauty clinics are everywhere to provide beauty spa. Since the spa devices, apparatus and products are various, the spa procedure, especially face spa, always needs a medical personnel to perform. Moreover, the spa devices and apparatus are always bulk which needs much space to put. Also, some of the spa devices or apparatus has to plug in the socket for use, that makes the spa device or apparatus can only be placed in a fixed position. As a result, a user has to move to different places when getting different treatments, which makes a user not be able to relax in treatment process and also leads to prolonged period of treatment. Thus, a spa mask which is configured to provide different wavelengths of light according to different types of faces of users is invented to overcome the problems mentioned above.

However, the conventional spa apparatus is disadvantageous because: (i) the spa mask is directly placed on the face of a user or hanged on the head of a user, when the treatment time is prolonged, the spa mask will cause discomfort to the user; and (ii) the radiation time and the wavelengths of light are required to be controlled by professional medical personnel, and it may result in anti-effect when the procedure goes wrong. Therefore, there remains a need for a new and improved design for a spa apparatus to overcome the problems presented above.

SUMMARY OF THE INVENTION

The present invention provides a spa apparatus which comprises a cart, a magnifying lamp, a phototherapy mask, a bed, and a bathtub. The cart has a plurality of first wheels installed at a bottom portion thereof, and a tabletop is formed at a top portion of the cart. Moreover, each of two sides of the tabletop has a tube-shaped handle which enables the cart to be pushed toward or away the bed for convenience to spa process. A computer, a storage battery, and a communicator are electrically connected and installed inside the cart, and the computer is electrically connected to a display which is firmly placed on the tabletop. The storage battery is electrically connected to a power outlet which is electrically connected to a power supply for charging the storage battery so as to enable the storage battery to provide power to the computer, the communicator and the display. The magnifying lamp comprises a first arm and a second arm, wherein a lower portion of the first arm is pivotally secured on the tabletop of the cart while a upper portion of the second arm is pivotally connected to a magnifier, and the connections between the tabletop and the first arm, and between the first arm and the second arm are respectively accomplished through a first pivot and a second pivot. An outer periphery of the magnifier has a first frame, and a ring lamp installed in the first frame is connected to a knob which is adapted to adjust the brightness of the ring lamp. The spa apparatus has the phototherapy mask which is formed in a human-face shape and has a plurality of openings at positions corresponding to human's eyes, nostril, and mouth. Also, a plurality of first LED phototherapy lamps and a plurality of skin sensors are scatteredly installed on an inner surface of the phototherapy mask, and the first LED phototherapy lamps and the skin sensors are electrically connected to a controller through a first wire. The controller has a supply wire which is configured to electrically connect to the power outlet of the cart. The controller has instant connection with the communicator of the cart through wireless communication. The modes of radiation of the first LED phototherapy lamps for skin care at least comprise blue-light wavelength (450-475 nm), green-light wavelength (495-570 nm), and red-light wavelength (620-750 nm). The phototherapy mask is pivotally connected to a second frame, and the second frame is sequentially and pivotally connected to a front arm, a rear arm and a base, and the connections between the front arm and the rear arm and between the rear arm and the base are respectively accomplished through a first pivot shaft and a second pivot shaft. Also, a plurality of second wheels are installed at a lower end of the base.

In one embodiment, the cart has at least a drawer and at least a spacing, and the drawer is divided into a plurality of rooms for placing small beauty products; the spacing is configured for placing the computer, the storage battery, the communicator, and large beauty products, and the spacing comprises at least a door.

In another embodiment, a table board formed between the tabletop and the drawer is configured to be slid out to become an extension of tabletop.

In still another embodiment, the computer and the storage battery are electrically connected to an auxiliary outlet which is mounted on the tabletop of the cart, and the auxiliary outlet has a plurality of two-prong outlets, three-prong outlets and USB holes to provide more options for electricity demands; a keyboard and a mouse are adapted to connect to the computer through the USB holes for operating the computer.

In a further embodiment, a plurality of shading pieces are installed on a periphery of the magnifier, and the first frame has a reel to control the shading area of the magnifier covered by the shading pieces.

In still a further embodiment, at least a quick-release member is connected between the phototherapy mask and the second frame, and the angle of the phototherapy mask is adapted to be quickly adjusted and fixed through pulling out and pushing back the quick-release member.

In an advantageous embodiment, a ball body cooperating with a cap is installed between the second frame and the front arm, and the ball body is configured to be rolled when the cap is loosen, thereby adjusting the use angle of the phototherapy mask; the first pivot shaft and the second pivot shaft are respectively cooperated with a first adjusting block and the a second adjusting block, and a first coil spring is connected between the first adjusting block and the front arm while a second coil spring is connected between the second adjusting block and the rear arm; a rod body is connected between the first adjusting block and the second adjusting block, and a telescopic rod is connected between the base and the rear arm.

In another advantageous embodiment, the controller of the phototherapy mask is connected to at least a mobile device through wireless communication, and after login in through the mobile device, a user is configured to receive personal treatment information including instant skin care status, beauty schedule, treatment record, product information, customer information during spa process.

In a preferred embodiment, the bathtub has a cover to cover the bathtub, and each of the bathtub and the cover comprises a plurality of water holes for hydro massage; a plurality of second LED phototherapy lamps installed on the cover are adapted to provide phototherapy to a user's body; the bathtub has a headrest so as to enable a user to have face treatment through the phototherapy mask at the same time.

In another preferred embodiment, the modes of radiation of the first LED phototherapy lamps for skin care further comprise violet-light wavelength (380-450 nm), blue-green-light wavelength (467-495 nm), and yellow-light wavelength (570-590 nm).

Comparing with conventional spa apparatus, the present invention is advantageous because: (i) the computer, the storage battery, and the communicator are installed in the cart, and the cart is electrically connected to the power outlet and the display, which enables the cart to be moved and used not limited by the location of power supply; (ii) the cart has the drawer and the spacing for the storage of beauty products and tools; (iii) with the front arm, the rear arm, and the base, the phototherapy mask is configured to be used in different angles and to be held above or in front of a user's in a preferable height; (iv) the computer is adapted to receive instant measured data from the skin sensors and adjust the radiation mode of first LED phototherapy lamps automatically or manually by a personnel or user according to the instant condition of user's skin; and (v) with the communicator, data including beauty schedule, treatment record, products information and customer information is adapted to transmit to cloud for backup and reading.

DETAILED DESCRIPTION OF THE INVENTION

Figure 1:
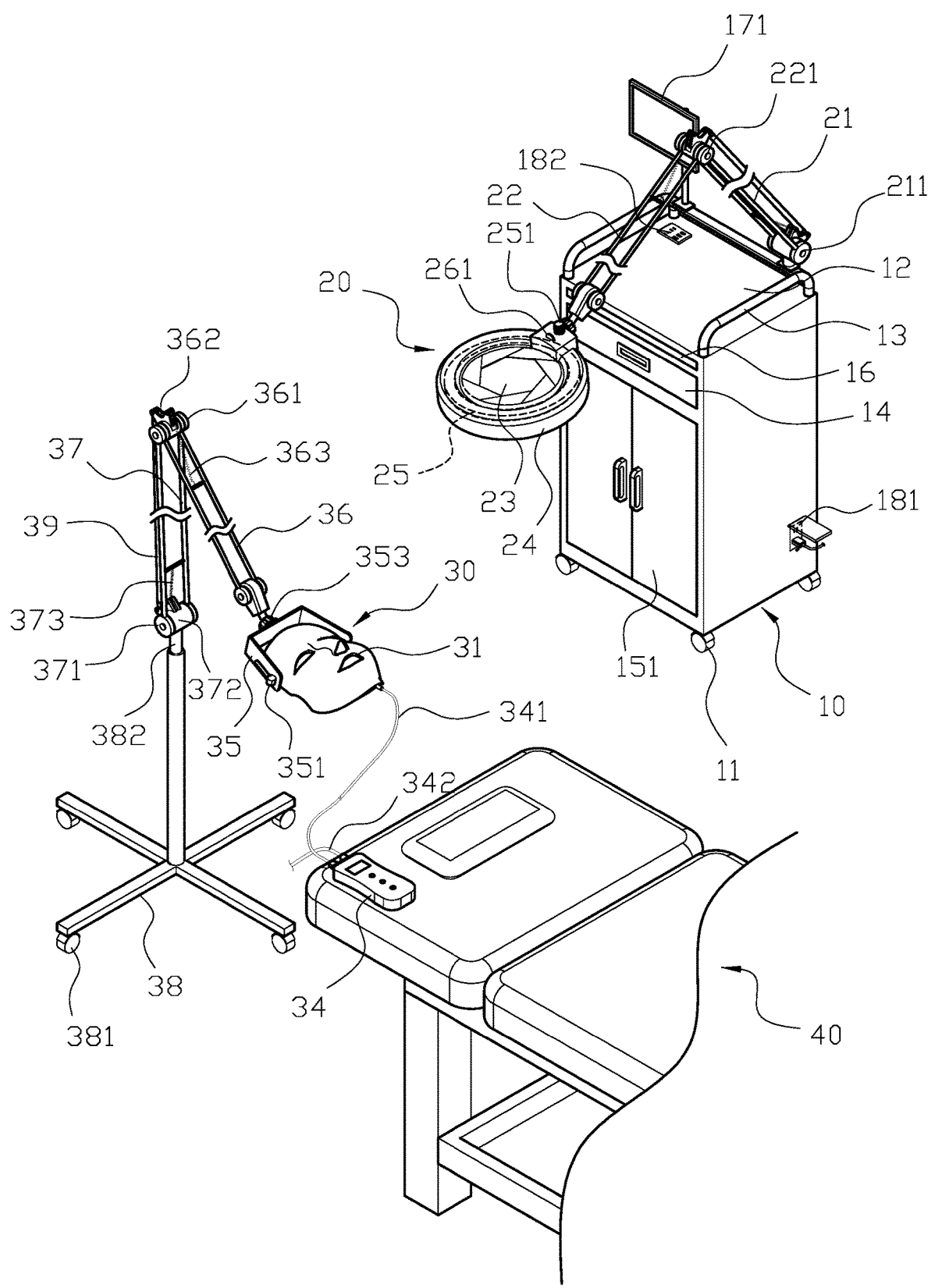
FIG. 1 is a three-dimensional assembly view of a spa apparatus of the present invention.
Figure 2:
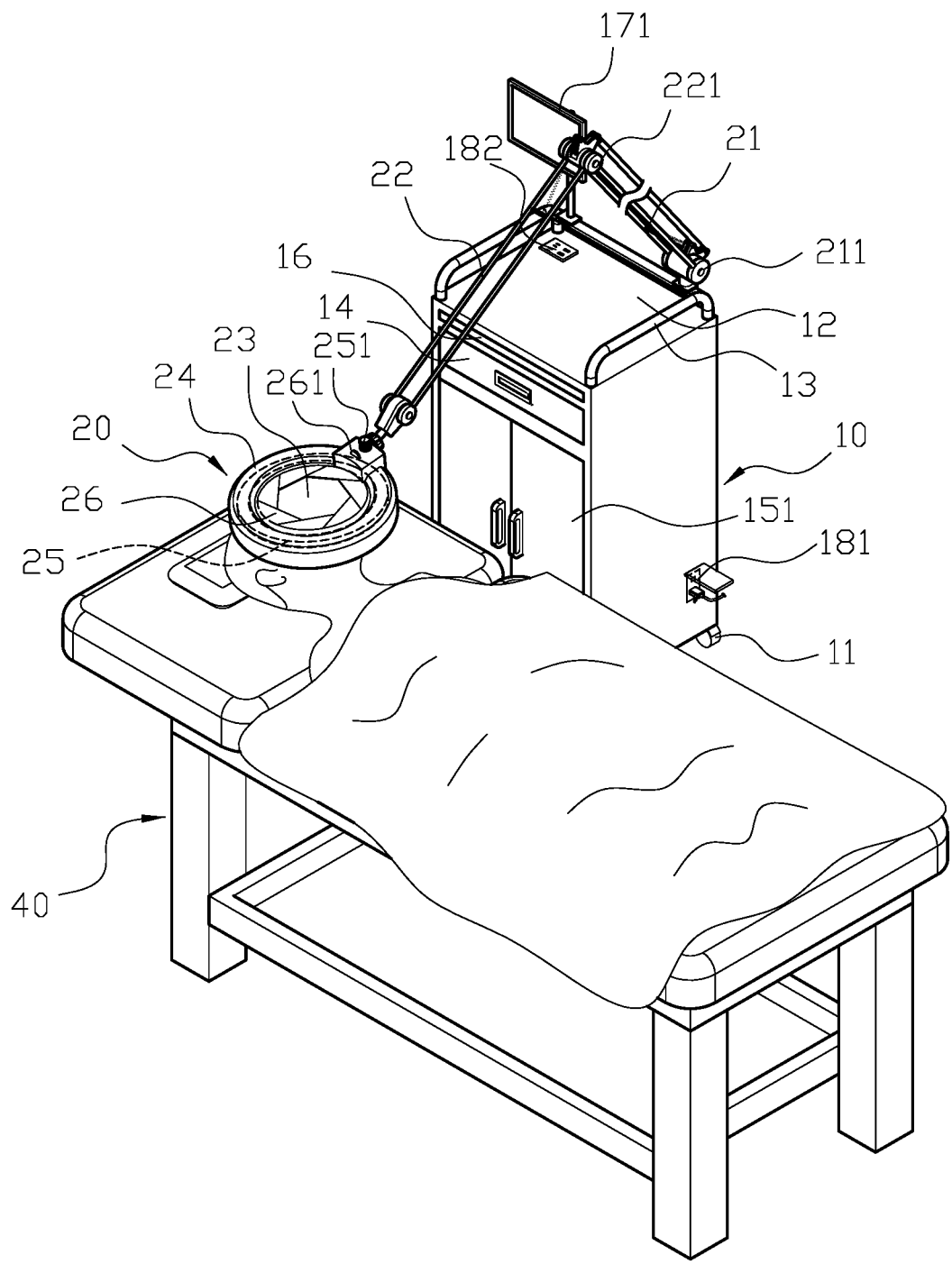
FIG. 2 is a three-dimensional schematic view illustrating the spa apparatus of the present invention is operated.
Figure 3:
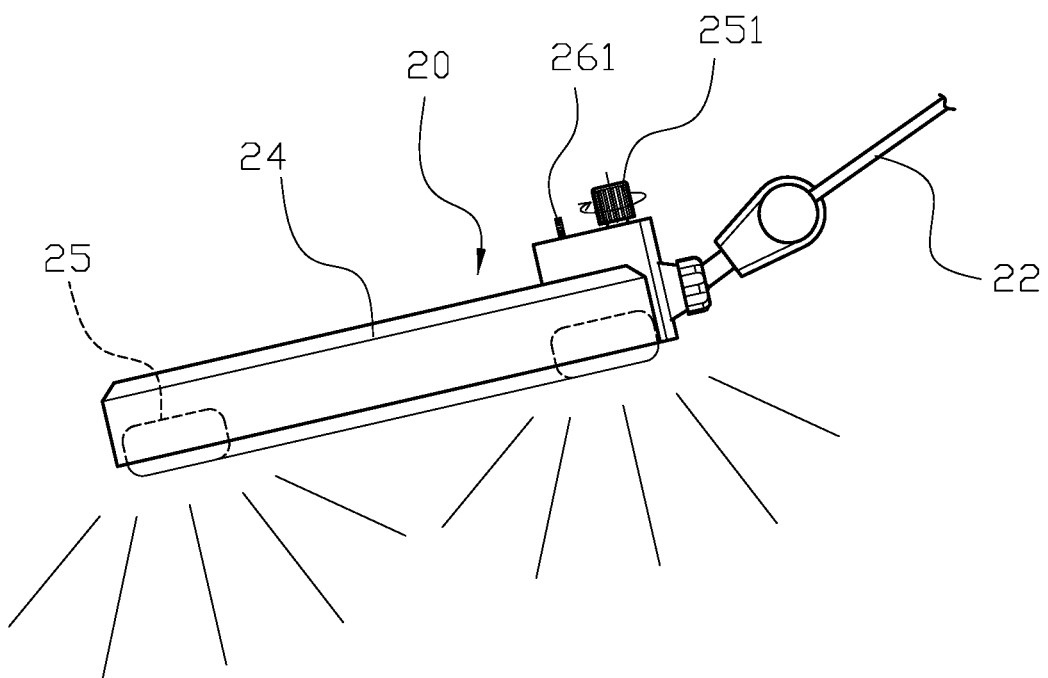
FIG. 3 is a side view of a magnifying lamp of the spa apparatus of the present invention.
Figure 4:
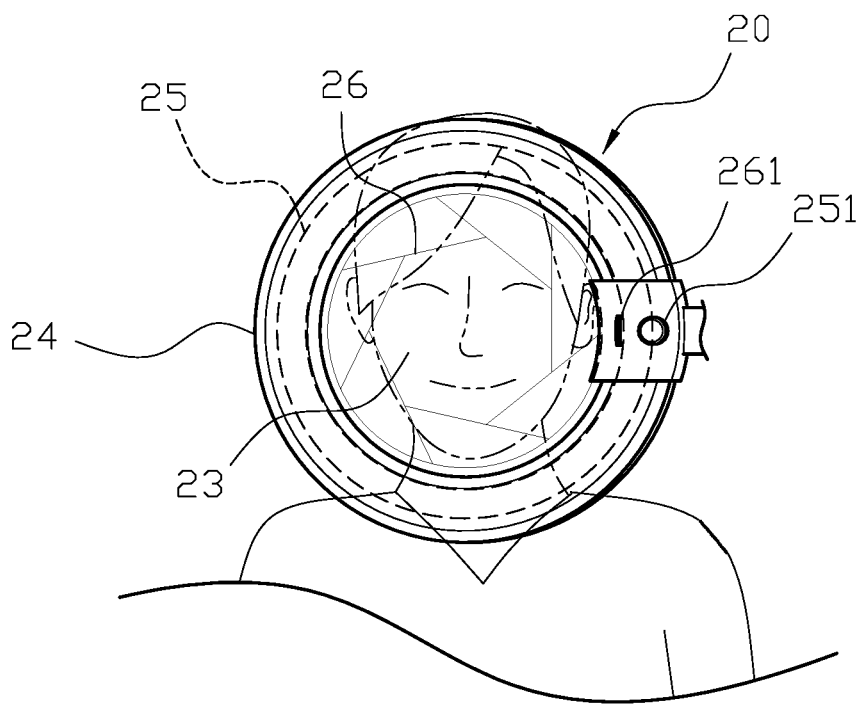
FIG. 4 is a schematic view illustrating the magnifying lamp of the spa apparatus of the present invention is in use.
Figure 5:
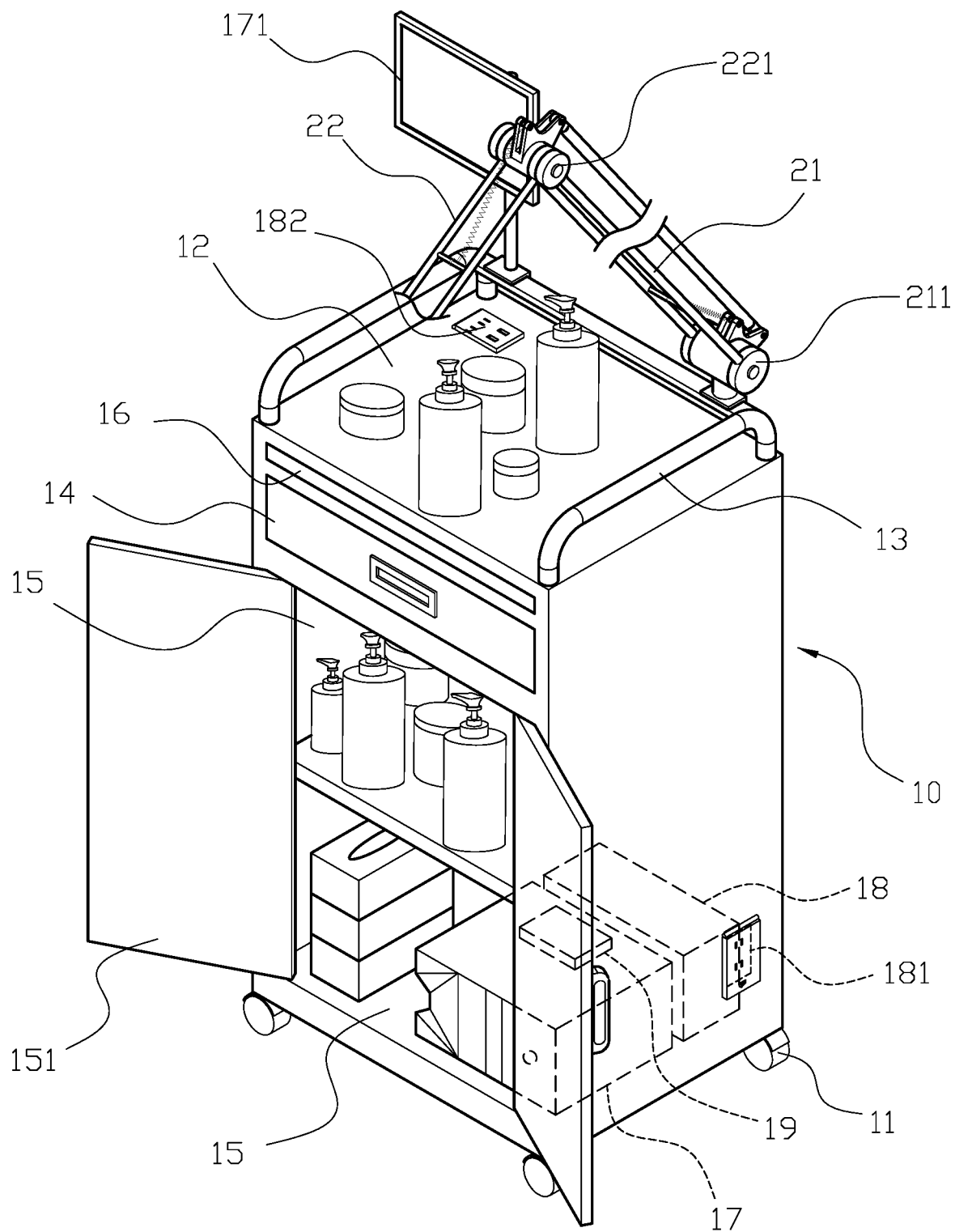
FIG. 5 is a schematic view illustrating a cart of the spa apparatus of the present invention is in use.
Figure 6:
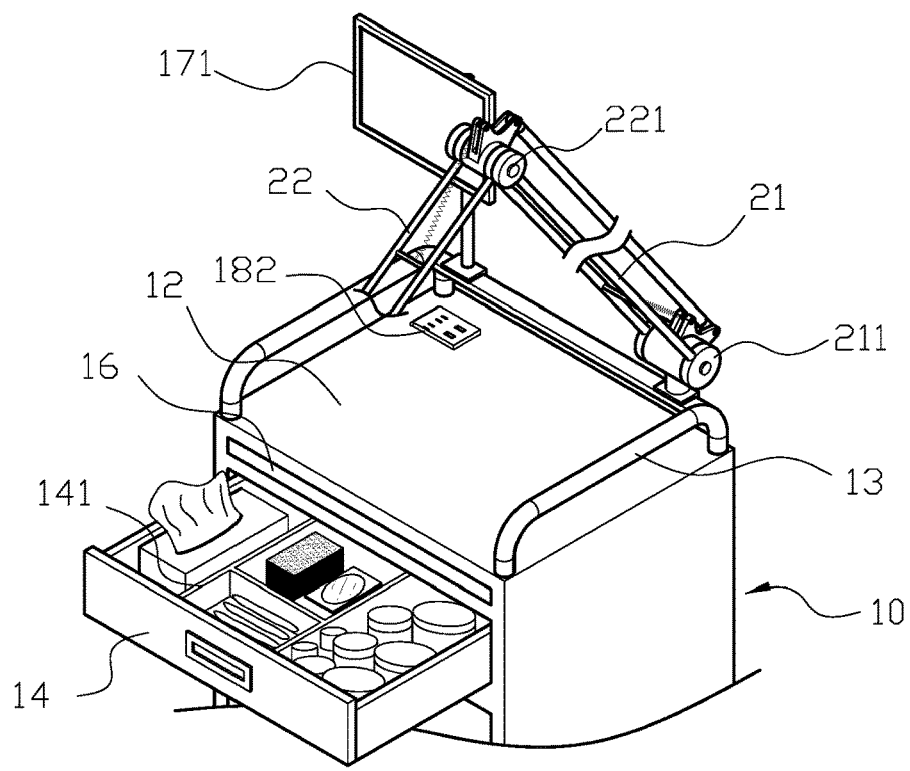
FIG. 6 is another schematic view illustrating the cart of the spa apparatus of the present invention is in use.
Figure 7:
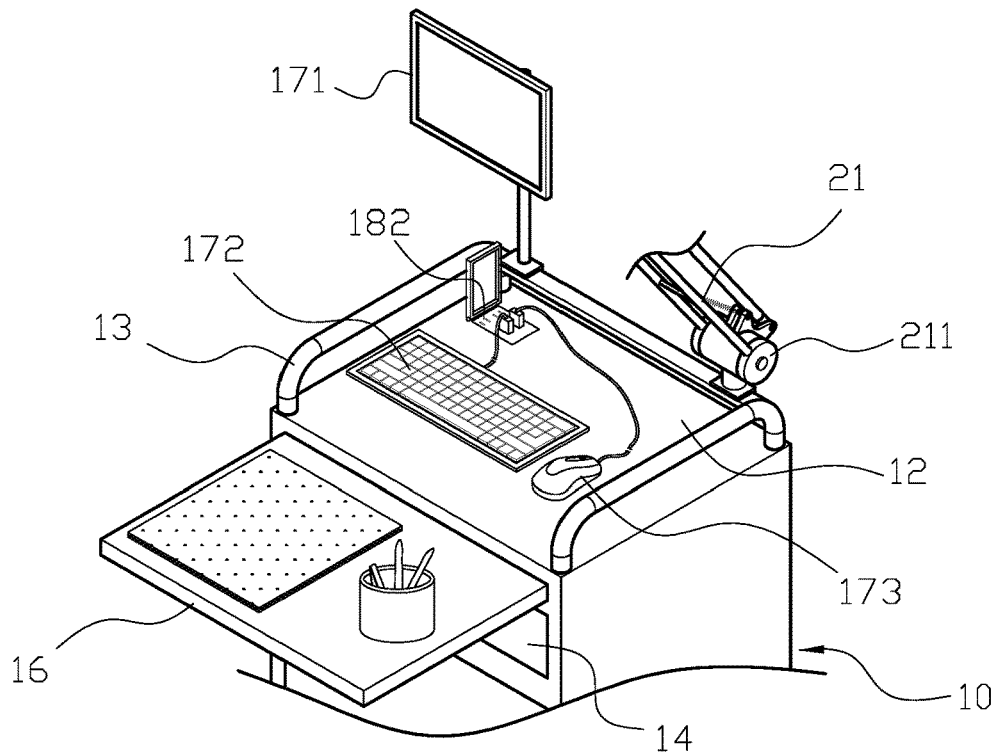
FIG. 7 is a third schematic view illustrating the cart of the spa apparatus of the present invention is in use.

The detailed description set forth below is intended as a description of the presently exemplary device provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described can be used in the practice or testing of the invention, the exemplary methods, devices and materials are now described.

All publications mentioned are incorporated by reference for the purpose of describing and disclosing, for example, the designs and methodologies that are described in the publications that might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

In order to further understand the goal, characteristics and effect of the present invention, a number of embodiments along with the drawings are illustrated as following:

Referring to FIGS. 1 to 7, the present invention provides a spa apparatus which comprises a cart (10), a magnifying lamp (20), a phototherapy mask (30), a bed (40), and a bathtub (50). The cart (10) has a plurality of first wheels (11) installed at a bottom portion thereof, and a tabletop (12) is formed at a top portion of the cart (10). Moreover, each of two sides of the tabletop (12) has a tube-shaped handle (13) which enables the cart (10) to be pushed toward or away the bed (40) for convenience to spa process, and the cart (10) has at least a drawer (14) and at least a spacing (15). Furthermore, the drawer (14) is divided into a plurality of rooms (141) for placing small beauty products such as essence, skin cream, paper towel, makeup remover pad, gloves, tongs and mirror, thereby keeping the drawer (14) neat. In addition, the spacing (15) is configured for placing large beauty products such as lotion bottle, essence bottle and tissue box, and the spacing (15) comprises at least a door (151). With the drawer (14) and the spacing (15) cooperating with door (151), the beauty products are adapted to be properly stored in the cart (10) when are not used. Also, a table board (16) formed between the tabletop (12) and the drawer (14) is configured to be slid out to become an extension of tabletop (12) so as to place more beauty products. Additionally, a computer (17), a storage battery (18), and a communicator (19) are electrically connected and installed inside the spacing (15) of the cart (10), and also the computer (17) is electrically connected to a display (171) which is firmly placed on the tabletop (12). The display (171) is adapted to show instant skin-care information during spa process, and the communicator (19) is configured to transmit data including beauty schedule, treatment record, products information and customer information to cloud for backup and reading. The storage battery (18) is electrically connected to a power outlet (181) which is electrically connected to a power supply for charging the storage battery (18) so as to enable the storage battery (18) to provide power to the computer (17), the communicator (19) and the display (171). Also, the storage battery (18) is adapted to be charged directly by an external power supply so as to enable the cart (10) to be moved and used not limited by the location of power supply. In addition, the computer (17) and the storage battery (18) are electrically connected to an auxiliary outlet (182) which is mounted on the tabletop (12) of the cart (10). The auxiliary outlet (182) has a plurality of two-prong outlets, three-prong outlets and USB holes to provide more options for electricity demands, and also a keyboard (172) and a mouse (173) are adapted to connect to the computer (17) through the USB holes for operating the computer (17). Furthermore, other auxiliary tools such as hair dryer, massager, mobile phone, essence light and fan are adapted to electrically connect to the auxiliary outlet (182) for use. The magnifying lamp (20) comprises a first arm (21) and a second arm (22), wherein a lower portion of the first arm (21) is pivotally secured on the tabletop (12) of the cart (10) while a upper portion of the second arm (22) is pivotally connected to a magnifier (23), and the connections between the tabletop (12) and the first arm (21), and between the first arm (21) and the second arm (22) are respectively accomplished through a first pivot (211) and a second pivot (221) so as to adjust the operating height, distance and angle of the magnifying lamp (20). An outer periphery of the magnifier (23) has a first frame (24), and a ring lamp (25) installed in the first frame (24) is connected to a knob (251) which is adapted to adjust the brightness of the ring lamp (25). In addition, a plurality of shading pieces (26) are installed on a periphery of the magnifier (23), and the first frame (24) has a reel (261) to control the shading area of the magnifier (23) covered by the shading pieces (26), thereby enabling light to focus on a specific portion of user's face and reducing reflected light irritating to eyes of the user. Also, the power of the ring lamp (25) is provided by the storage battery (18).

Referring to FIGS. 1, 5, 8 and 9, the spa apparatus has the phototherapy mask (30) which is formed in a human-face shape and has a plurality of openings (31) at positions corresponding to human's eyes, nostril, and mouth. Also, a plurality of first LED phototherapy lamps (32) and a plurality of skin sensors (33) are scatteredly installed on an inner surface of the phototherapy mask (30), and the first LED phototherapy lamps (32) and the skin sensors (33) are electrically connected to a controller (34) through a first wire (341). Furthermore, the controller (34) has a supply wire (342) which is configured to, but not limited to, electrically connect to the power outlet (181) of the cart (10). The phototherapy mask (30) is adapted to cover a user's face, and the openings (31) are configured to keep the user's eyes, nostril, and mouth exposed, which enables the user to see and talk during spa process. The controller (34) has instant connection with the communicator (19) of the cart (10) through wireless communication such that the computer (17) is adapted to receive instant measured data from the skin sensors (33) and adjust the radiation mode of first LED phototherapy lamps (32) automatically or manually by a personnel or user according to the instant condition of user's skin. The modes of radiation for skin care at least comprise violet-light wavelength (380-450 nm), blue-light wavelength (450-475 nm), blue-green-light wavelength (467-495 nm), green-light wavelength (495-570 nm), yellow-light wavelength (570-590 nm) and red-light wavelength (620-750 nm). Through the phototherapy mask (30), the different modes of radiation can provide a user with different skin care effects including improving cells activity, accelerating metabolism, decomposing melanin, inhibiting inflammation, whitening skin, repairing damaged skin, tightening skin, neutralizing oil secretion, and anti-aging. Moreover, the skin sensors (33) are configured to monitor the spa process, thereby recording beauty history and optimizing skin care process. Furthermore, the phototherapy mask (30) is pivotally connected to a second frame (35), and at least a quick-release member (351) is connected between the phototherapy mask (30) and the second frame (35). The angle of the phototherapy mask (30) is adapted to be quickly adjusted and fixed through pulling out and pushing back the quick-release member (351). In addition, the second frame (35) is sequentially and pivotally connected to a front arm (36), a rear arm (37) and a base (38), and the connections between the front arm (36) and the rear arm (37) and between the rear arm (37) and the base (38) are respectively accomplished through a first pivot shaft (361) and a second pivot shaft (371). Thus, with the first pivot shaft (361), the second pivot shaft (371), and the quick-release member (351), the phototherapy mask (30) is configured to be held above or in front of a user's face in a preferable height, distance and angle, thereby improving treatment comfort for a user and enabling a user to have treatment in sitting posture. Furthermore, a plurality of second wheels (381) installed at a lower end of the base (38) are adapted to enable the phototherapy mask (30) to be portably used around the bed (40), which improves the convenience of spa process. A ball body (352) cooperating with a cap (353) is installed between the second frame (35) and the front arm (36), and the ball body (352) is configured to be rolled when the cap (353) is loosen, thereby adjusting the use angle of the phototherapy mask (30). Also, the first pivot shaft (361) and the second pivot shaft (371) are respectively cooperated with a first adjusting block (362) and the a second adjusting block (372), and a first coil spring (363) is connected between the first adjusting block (362) and the front arm (36) while a second coil spring (373) is connected between the second adjusting block (372) and the rear arm (37). Additionally, a rod body (39) connected between the first adjusting block (362) and the second adjusting block (372) is adapted to cooperatively support the front arm (36) and the rear arm (37) with the first coil spring (363) and the second coil spring (373). Moreover, a telescopic rod (382) connected between the base (38) and the rear arm (37) is configured to extend relative to the base (38), thereby adjusting height of the phototherapy mask (30). The controller (34) of the phototherapy mask (30) is connected to at least a mobile device (30A) through wireless communication, and after login in through the mobile device (30A), a user can receive personal treatment information including instant skin care status, beauty schedule, treatment record, product information, customer information during spa process and can remotely control the controller (34) to change radiation mode of the phototherapy mask (30). The mobile device (30A) is configured to be operated by a user or a professional medical personnel, and functions in mobile device (30A) are selectively available according to login user and account permission.

Figure 8:
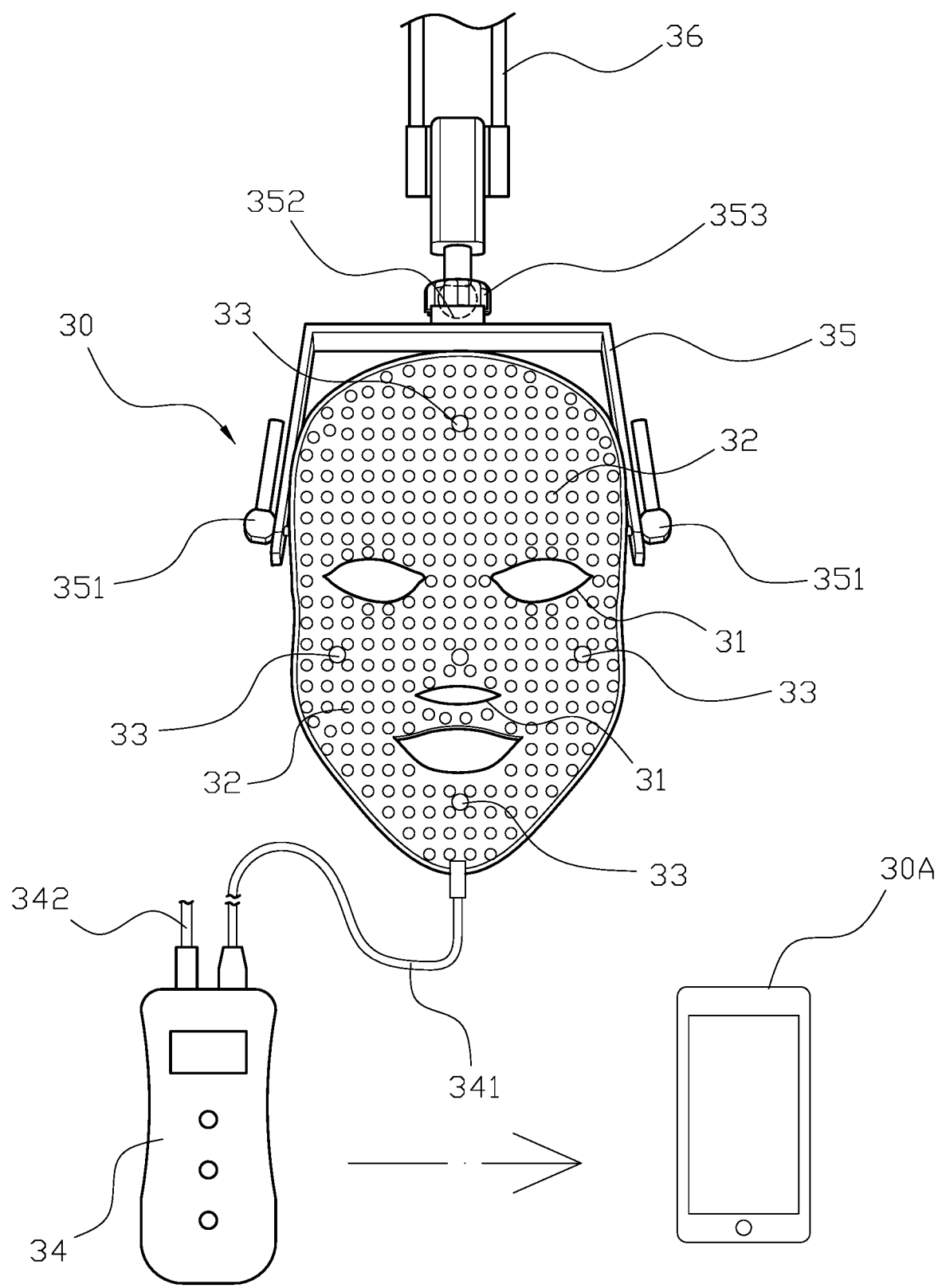
FIG. 8 is a schematic view of an inner surface of a phototherapy mask of the spa apparatus of the present invention.
Figure 9:
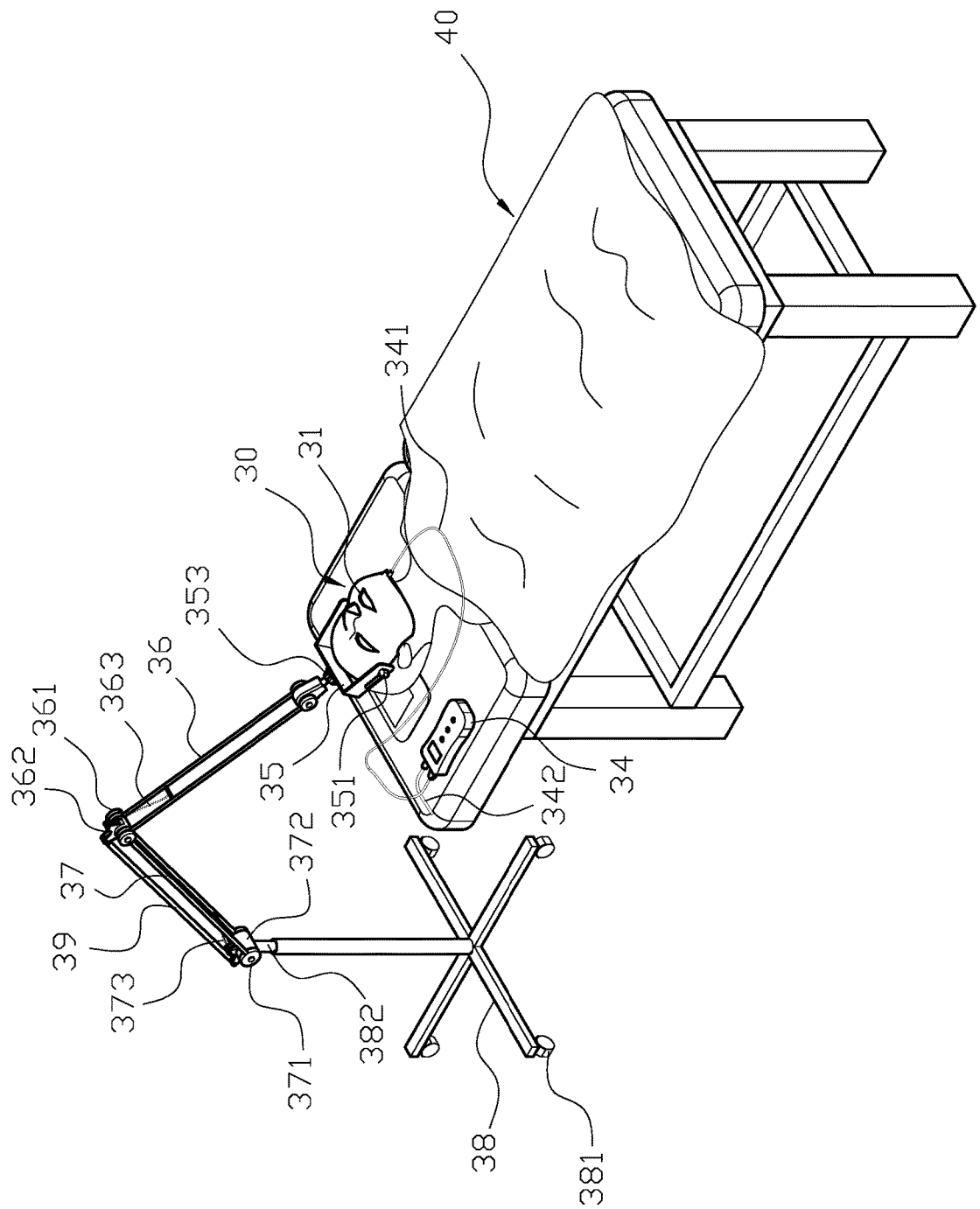
FIG. 9 is a three-dimensional schematic view illustrating the phototherapy mask of the spa apparatus of the present invention is in use.
Figure 10:
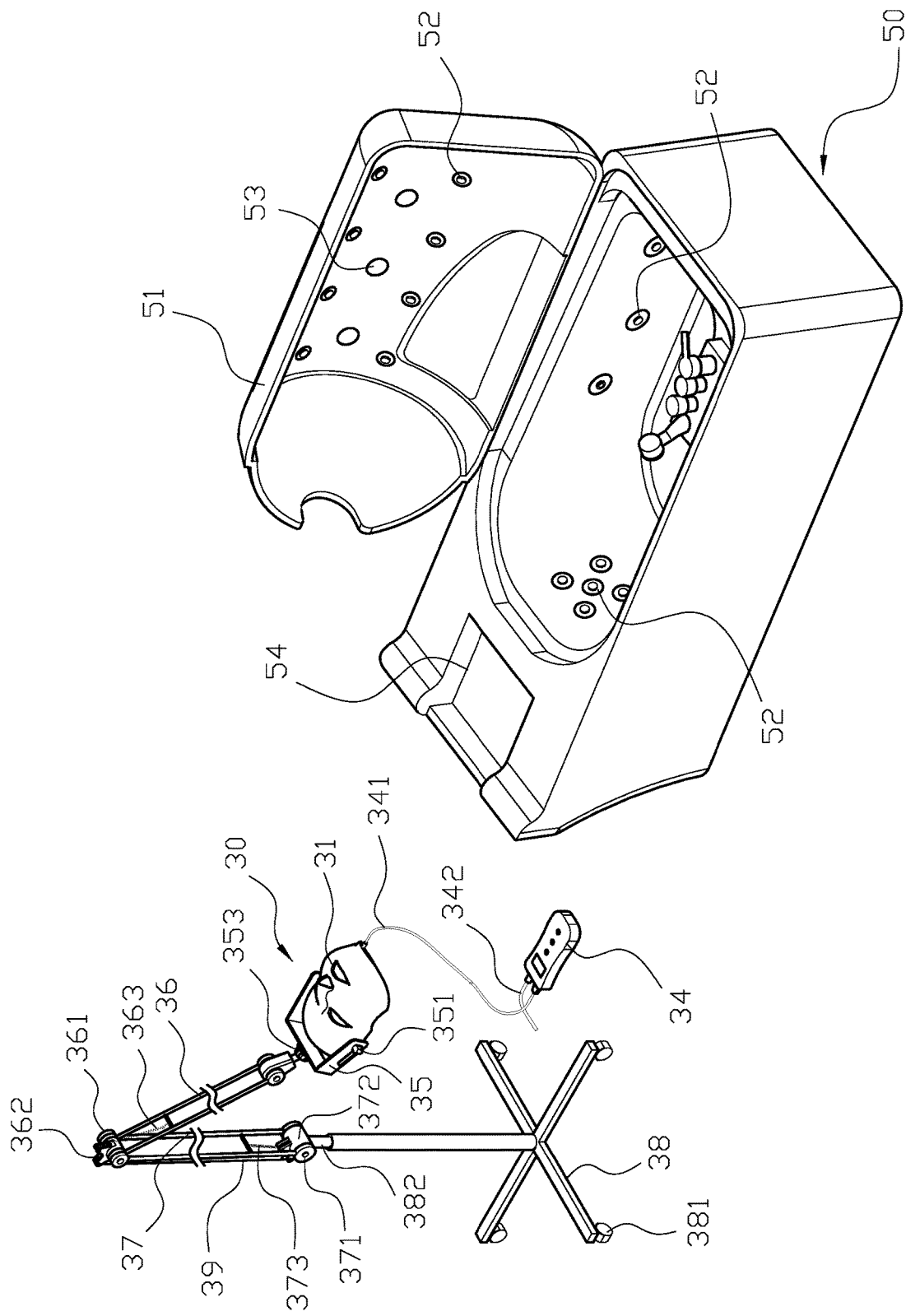
FIG. 10 is a three-dimensional view illustrating the phototherapy mask is cooperatively used with a bathtub of spa apparatus of the present invention.
Figure 11:
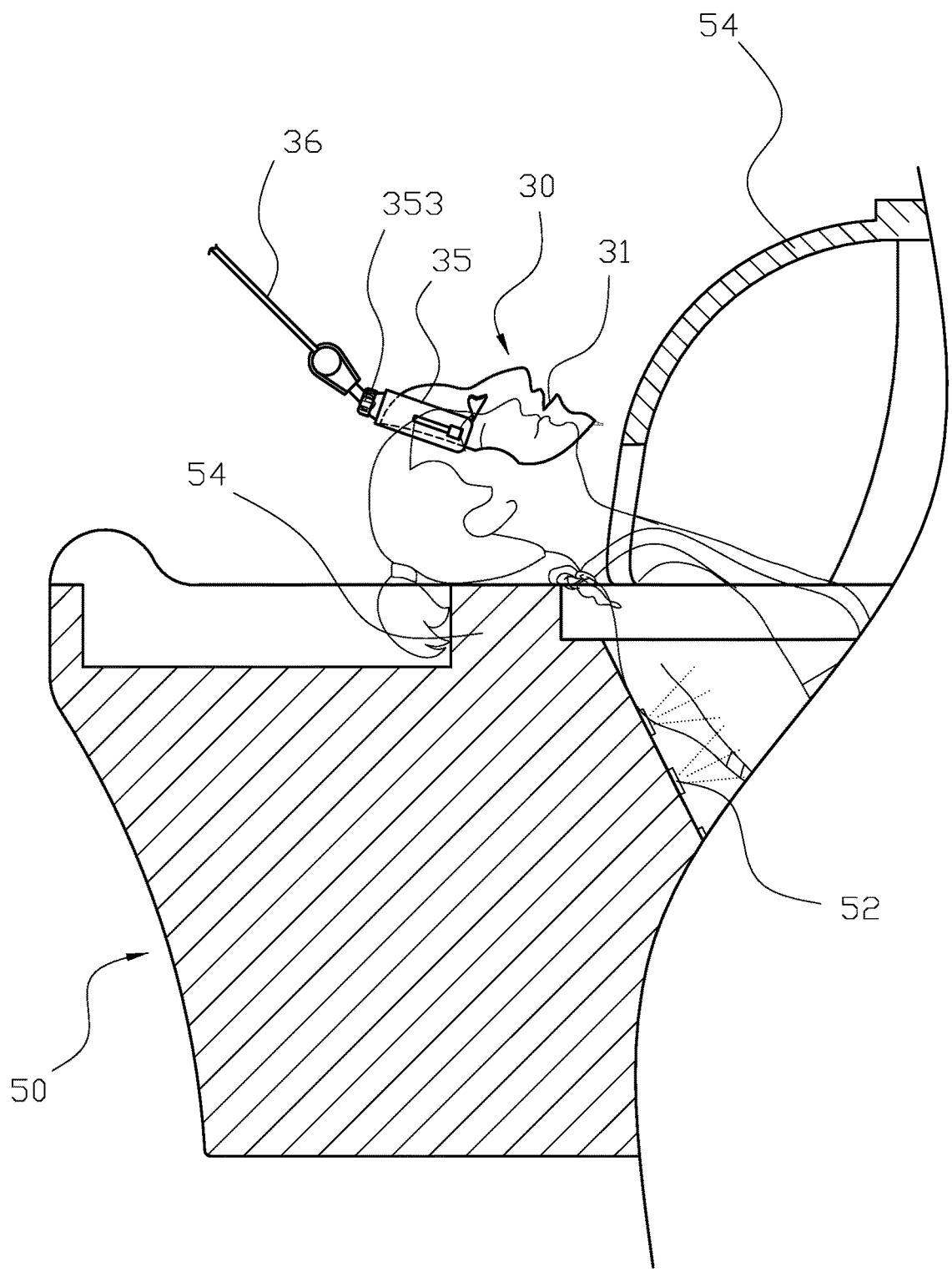
FIG. 11 is a schematic view illustrating the phototherapy mask is cooperatively used with the bathtub of spa apparatus of the present invention.

Referring to FIGS. 8, 10 and 11, the bathtub (50) has a cover (51) to cover the bathtub (50), and each of the bathtub (50) and the cover (51) comprises a plurality of water holes (52) for hydro massage. Also, a plurality of second LED phototherapy lamps (53) installed on the cover (51) are adapted to provide phototherapy to a user's body, thereby achieving the effects including improving cells activity, accelerating metabolism, decomposing melanin, relieving stress, removing edema, and strengthening immune system. Furthermore, the bathtub (50) has a headrest (54) so as to enable a user to have face treatment through the phototherapy mask (30) at the same time, thereby reducing the treatment time.

Having described the invention by the description and illustrations above, it should be understood that these are exemplary of the invention and are not to be considered as limiting. Accordingly, the invention is not to be considered as limited by the foregoing description, but includes any equivalents.

What is claimed is:

1. A spa apparatus comprising
a cart having a plurality of first wheels installed at a bottom portion thereof, and a tabletop formed at a top portion of the cart; each of two sides of the tabletop having a tube-shaped handle which enables the cart to be pushed toward or away a bed for convenience to spa process; a computer, a storage battery, and a communicator electrically connected and installed inside the cart, and the computer electrically connected to a display which is firmly placed on the tabletop; the display adapted to show instant skin-care information during spa process, and the communicator configured to transmit data including beauty schedule, treatment record, products information and customer information to CLOUD for backup and reading thereafter; the storage battery electrically connected to a power outlet which is electrically connected to a power supply for charging the storage battery so as to enable the storage battery to provide power to the computer, the communicator and the display; a magnifying lamp comprising a first arm and a second arm, wherein a lower portion of the first arm is pivotally secured on the tabletop of the cart while a upper portion of the second arm is pivotally connected to a magnifier, and the connections between the tabletop and the first arm, and between the first arm and the second arm are respectively accomplished through a first pivot and a second pivot so as to adjust the operating height, distance and angle of the magnifying lamp; an outer periphery of the magnifier having a first frame, and a ring lamp, which is installed in the first frame, connected to a knob which is adapted to adjust brightness of the ring lamp; power of the ring lamp provided by the storage battery, which enables the cart to be moved and used not limited by the location of power supply; and
a phototherapy mask formed in a human-face shape and having a plurality of openings at positions corresponding to human's eyes, nostril, and mouth; a plurality of first LED phototherapy lamps and a plurality of skin sensors scatteredly installed on an inner surface of the phototherapy mask, and the first LED phototherapy lamps and the skin sensors electrically connected to a controller through a first wire; the controller having a supply wire which is configured to electrically connect to the power outlet of the cart; the controller having connection with the communicator of the cart through wireless communication such that the computer adapted to receive instant measured data from the skin sensors and adjust the radiation mode of first LED phototherapy lamps automatically or manually by a personnel or user according to the instant condition of user's skin; the modes of radiation of the first LED phototherapy lamps for skin care at least comprising blue-light wavelength (450-475 nm), green-light wavelength (495-570 nm), and red-light wavelength (620-750 nm); the phototherapy mask pivotally connected to a second frame, and the second frame sequentially and pivotally connected to a front arm, a rear arm and a base, wherein the connections between the front arm and the rear arm and between the rear arm and the base are respectively accomplished through a first pivot shaft and a second pivot shaft such that the phototherapy mask configured to be held above a user's face in a preferable height, distance and angle, thereby improving treatment comfort for a user; a plurality of second wheels are installed at a lower end of the base to enable the phototherapy mask to be portably used around the bed.

2. The spa apparatus of claim 1, wherein the cart has at least a drawer and at least a spacing, and the drawer is divided into a plurality of rooms for placing cosmetics; the spacing is configured for placing the computer, the storage battery, the communicator, and large beauty products, and the spacing comprises at least a door.

3. The spa apparatus of claim 1, wherein a table board formed between the tabletop and the drawer is configured to be slid out to become an extension of tabletop.

4. The spa apparatus of claim 1, wherein the computer and the storage battery are electrically connected to an auxiliary outlet which is installed on the tabletop of the cart, and the auxiliary outlet has a plurality of two-prong outlets, three-prong outlets and USB holes to provide more options for electricity demands; a keyboard and a mouse are adapted to connect to the computer through the USB holes for operating the computer.

5. The spa apparatus of claim 1, wherein a plurality of shading pieces are installed on a periphery of the magnifier, and the first frame has a reel to control the shading area of the magnifier covered by the shading pieces.

6. The spa apparatus of claim 1, wherein at least a quick-release member is connected between the phototherapy mask and the second frame, and the angle of the phototherapy mask is adapted to be quickly adjusted and fixed through pulling out and pushing back the quick-release member.

7. The spa apparatus of claim 1, wherein a ball body cooperating with a cap is installed between the second frame and the front arm, and the ball body is configured to be rolled when the cap is loosen, thereby adjusting the use angle of the phototherapy mask; the first pivot shaft and the second pivot shaft are respectively cooperated with a first adjusting block and the a second adjusting block, and a first coil spring is connected between the first adjusting block and the front arm while a second coil spring is connected between the second adjusting block and the rear arm; a rod body is connected between the first adjusting block and the second adjusting block, and a telescopic rod is connected between the base and the rear arm.

8. The spa apparatus of claim 1, wherein the controller of the phototherapy mask is connected to at least a mobile device through wireless communication, and after login in through the mobile device, a user is configured to receive personal treatment information including instant skin care status, beauty schedule, treatment record, product information, customer information during spa process.

9. The spa apparatus of claim 1, wherein a bathtub has a cover to cover the bathtub, and each of the bathtub and the cover comprises a plurality of water holes for hydro massage; a plurality of second LED phototherapy lamps installed on the cover are adapted to provide phototherapy to a user's body; the bathtub has a headrest so as to enable a user to have face treatment through the phototherapy mask at the same time.

10. The spa apparatus of claim 1, wherein the modes of radiation of the first LED phototherapy lamps for skin care comprise violet-light wavelength (380-450 nm), blue-green-light wavelength (467-495 nm), and yellow-light wavelength (570-590 nm).

* * * * *